United States Patent [19]

Dickey

[11] Patent Number: 4,599,225
[45] Date of Patent: * Jul. 8, 1986

[54] CONTINUOUS FLOW SEPARATION WITH MOVING BOUNDARY SORPTION

[75] Inventor: Leland C. Dickey, Omaha, Nebr.

[73] Assignee: InterNorth, Inc., Omaha, Nebr.

[*] Notice: The portion of the term of this patent subsequent to Oct. 22, 2002 has been disclaimed.

[21] Appl. No.: 752,097

[22] Filed: Jul. 5, 1985

Related U.S. Application Data

[63] Continuation of Ser. No. 561,899, Dec. 15, 1983, abandoned.

[51] Int. Cl.$^4$ .................... B01D 15/02; B01D 15/08
[52] U.S. Cl. ............................ 423/659; 55/34; 55/67; 55/77; 55/181; 55/390; 210/656; 210/670; 210/671; 210/673; 210/198.2; 423/210
[58] Field of Search .................. 55/34, 67, 77–79, 55/99, 181, 386, 390; 423/219, 242 A, 659, 210 R, 210 S; 210/656–659, 660, 670, 671, 676; 422/70; 435/70, 174, 183, 184, 287, 803

[56] References Cited

U.S. PATENT DOCUMENTS

| | | | |
|---|---|---|---|
| 2,222,828 | 11/1940 | Guthrie | 55/390 |
| 2,302,807 | 11/1942 | Shoeld | 55/390 |
| 2,639,000 | 5/1953 | Edwards | 184/4.6 |
| 2,678,132 | 5/1954 | Beard | 210/670 |
| 3,335,081 | 8/1967 | El-Nagger | 210/619 |
| 3,498,026 | 3/1970 | Messinger | 55/390 |
| 3,598,726 | 8/1971 | Welch | 210/619 |
| 3,757,492 | 5/1971 | Graff | 55/181 |
| 3,907,967 | 9/1975 | Filss | 423/210 S |
| 4,083,778 | 4/1978 | McGrew | 210/671 |
| 4,242,107 | 12/1980 | Jenkins | 55/390 |
| 4,292,054 | 9/1981 | Noack | 55/181 |
| 4,302,222 | 11/1981 | Miller | 55/390 |
| 4,324,564 | 4/1982 | Oliker | 55/20 |
| 4,348,290 | 9/1982 | Schipper | 210/783 |
| 4,351,650 | 9/1982 | Shinoda | 55/181 |
| 4,353,720 | 10/1982 | Margraf | 55/262 |
| 4,391,616 | 7/1983 | Imamura | 55/390 |
| 4,415,342 | 11/1983 | Foss | 55/96 |

Primary Examiner—Ernest G. Therkorn
Attorney, Agent, or Firm—Donald F. Haas

[57] ABSTRACT

A continuous process for separating components of a fluid mixture is disclosed which comprises forming a sorption zone and a desorption zone, said zones being separated by a boundary of a sorbent material which continuously moves back and forth between the zones, causing a fluid mixture to flow into the sorption zone wherein the conditions are such to promote sorption of one of the components of the mixture by the sorbent material, and creating conditions in the desorption zone such that the sorbed component will be desorbed when the sorbent material containing the sorbed component moves into the desorption zone.

4 Claims, 4 Drawing Figures

4,599,225

CONTINUOUS FLOW SEPARATION WITH MOVING BOUNDARY SORPTION

This is a continuation of application Ser. No. 561,899 filed Dec. 15, 1983, now abandoned.

BACKGROUND OF THE INVENTION

This invention relates to a continuous process for obtaining optimal separation of a fluid mixture by sorption. The method also relates to a process for preparing precise fluid mixtures where the metered component is mixed by moving boundary sorption.

In recent years, cyclic separation processes have received considerable attention. Such processes as pressure-swing adsorption, parametric pumping, and cycling zone adsorption, separate continuous or semi-continuous fluid feed streams by cycling a thermodynamic variable which affects the mass transfer of fluid components with a sorption media. The cycle is designed to alternately sorb and desorb components so the fluid components are separated and the media returns to its initial condition after the completion of a cycle. The feed and product streams can be rendered continuous by combining sorption units in parallel but each unit necessarily experiences discontinuous flow conditions so that the sorbing media can be altered by changing thermodynamic variables such as temperature, pH, or pressure, for example, and so that the other product stream can be created thereby. The discontinuity of flow through or past the sorbing media creates inefficiency in the separations because of the mixing of fluid elements that have been exposed to the sorbing media under different conditions.

All practical separation techniques that occur with discontinuous flow result in product reservoir mixing. Since the feed mixture flows through the vessel during the sorption cycle of the cycling process, the sorbent will fill with the sorbed fluid component and the sorptivity will decrease. Thus, fluid entering the vessel early in the cycle is stripped of the sorbable constitutents to a greater extent than fluid entering late in the cycle. As a result, the composition of the fluid emerging from the sorbent zone is continually changing. Such a system cannot be controlled as efficiently as a single condition, continuous, time invariant process because in the cyclic operation you must compromise between optimizing for the early portion of the sorption cycle and the later portion. The ideal situation where product flow streams are not mixed would require a prohibitively large number of separate reservoirs as well as a complicated flow management system.

It is an object of the present invention to provide a method for continuous flow separation or mixing which avoids the inefficiences inherent in reservoir mixing. It is a further object of the present invention to provide a continuous method of flow separation or mixing wherein the only seal between the sorption and desorption zones is the sorption media itself.

SUMMARY OF THE INVENTION

The present invention relates to a continuous process for separating components of a fluid mixture which comprises first forming a sorption zone and a desorption zone. The two zones are separated by a boundary of a sorbent material which continuously moves back and forth between the zones. A fluid mixture is caused to flow into the sorption zone wherein the conditions are such to promote sorption of one of the components of the mixture by the sorbent material. Finally, conditions are created in the desorption zone such that the sorbed component will be desorbed when the sorbent material containing it moves into the desorption zone. In a preferred embodiment of the present invention, there is disposed between the two zones a series of rotating rollers which have the sorbent material at least on the surfaces thereof and which are in engagement in series so that the sorbent material forms the boundary between the two zones. The numbers of rollers is necessarily even and four or more. The rollers need not all be alike or even symmetrical so long as they form a boundary composed of rotatable elements.

In another embodiment of the present invention, the desorbed component forms a part of a second fluid mixture which is present in the desorption zone. In such a situation, the desorption zone can be a reaction zone wherein the rate of reaction is controlled by the amount of desorbed component which enters the desorption zone.

DETAILED DESCRIPTION OF THE INVENTION

Figure 2:
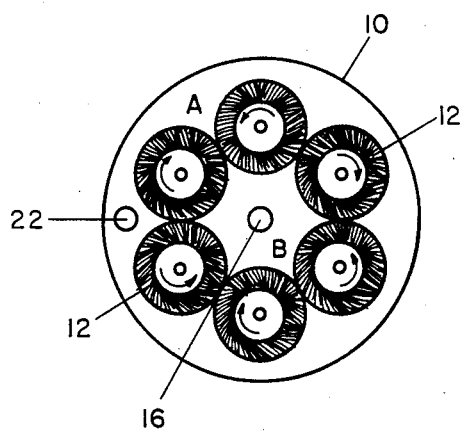
FIG. 2 is a cross section of an apparatus containing six soft rollers which are either constructed of a sorbent material or are coated with such a material.

As stated above, the process of the present invention provides a continuous method for separating components of a fluid mixture. The invention requires that separate chambers be connected by a rotatable sorbent barrier which will continuously alternate the sorbent face exposed to each chamber. The rotation rate will be varied to optimize separation in conjunction with the fluid stream throughput and the sorption/desorption conditions.

As stated above, a fluid mixture is caused to flow into the sorption zone wherein the conditions are such to promote sorption of one of the components of mixture by the sorbent material. Then conditions are created in the desorption zone to promote the desorbing of the sorbed component when the sorbent material containing it moves into the desorption zone. Thermodynamic variables such as temperature and pressure can be used to influence the sorption and desorption of the component of the original fluid mixture. Other variables such as pH, concentration of other chemical species, or voltage can also be used to influence the sorption/desorption process. Examples of fluid separations which can be performed according to the method of the present invention are aqueous acetic acid, aqueous glucose and fructose, enzyme mixtures in aqueous solution, dipeptides in aqueous solution, and any gas mixture where one component or group of components can be selectively sorbed. Hydrogen and water can be readily removed from nonpolar gases such as power plant exhaust gases.

The process of the present invention can also be used to mix fluid components together. The mixing mode is useful in preparing precise fluid mixtures where the metered component is carried into the desorption or product chamber by the sorbent material. The product chamber might in fact be a reaction chamber where the feed of the sorbent-carried reactant is rate controlling. An example of this is partial oxidation of hydrocarbons in which oxygen is transported from an air chamber to a reaction chamber by a sorbent material. In this case, both chambers could be at high pressure because the absorbed oxygen would be desorbed by reaction rather than partial pressure reduction as in the case of other fluid separations. The pressure of the two chambers should be nearly equal to minimize gas leakage or pumping by the moving elements.

For purposes of this invention sorbent materials are generally of four types:
1. Solids which can absorb gases in the bulk of the material. For example $FeTi$, $LaNi_5$, and the other so-called metal hydrides can absorb hydrogen. Solids with a high specific surface such as Fuller's earths, bauxite, alumina, gas adsorbent carbon, silica gel and zeolites (aluminosilicates) can be used. In some of these latter examples considerable temperature elevation is required to regenerate the adsorptivity. This might necessitate some modification of the apparatus design so that the desorption chambers can withstand the heat.
2. Porous insoluble solids containing absorbent liquids, such as carboxy-methyl cellulose, (CMC)/water, or saponified starch-g-polyacrylonitrile, (HSPAN)/water, can be used. In either case the water is strongly bound to the solid but is still as absorptive as pure water. Other polar solvents or aqueous solutions could be used with these solids (CMC or HSPAN) but it is likely that modification of the constituent solid would be the preferred way to optimize a particular gas absorption application. Generally, the polarity of the solid should match that of the chosen absorbent liquid to maximize liquid content in the sorbent combination. Consequently, various hydrocarbon-swellable polyolefins would provide suitable mechanical support for alkanes or other nonpolar liquids.
3. Gels formed from solvents and soluble solids such as polymers of soluble monomers can also be used. The distinction from (2) is that in this case the solid does not provide any structural form and therefore the gel can be applied as a coating to an existing solid or possibly cast into appropriate form. Examples are protein/water, cellulose acetate/water, ABS polymers/ketones, and polystyrene/aromatic solvents.
4. Solids formed from a combination of fluids that solidify under conditions in the sorption chamber, especially where one of the fluids is the sorbed component, can be used. This is the most complicated case from the standpoint of designing a process in which the sorption phase seals the chambers. However, it is the only one where elasticity of the sorbent will not be necessary to achieve a tight fit between the moving elements. Examples would be hydrate formation or reversible polymerization of a fluid monomer being removed from a mixture with nonpolymerizable components. It is possible that if one of the combining components is more or less permanently fixed to the moving element, e.g. water in the case of hydrate formulation, it could be supported in or with a solid material such as cases (2) and (3) above.

It is very important to the present invention that the sorbent material provides the seal which separates the sorption zone from the desorption zone. In order to accomplish this, the sorbent material or support for the sorbent material may be deformable so that it can provide an acceptable seal. In one embodiment of this invention, the separation between the two zones is provided by a series of rotating rollers which have the sorbent material at least on the surfaces thereof and which are in engagement in series so that the sorbent material forms the boundary between the two zones. The configuration of the rollers can be circular or linear or other as long as at least two distinct zones are formed thereby. If the sorbent material is not deformable, then it is important that the rollers underlying or otherwise supporting the sorbent be deformable. It is possible to use a gear-like structure in place of rollers in a similar arrangement.

Figure 1:
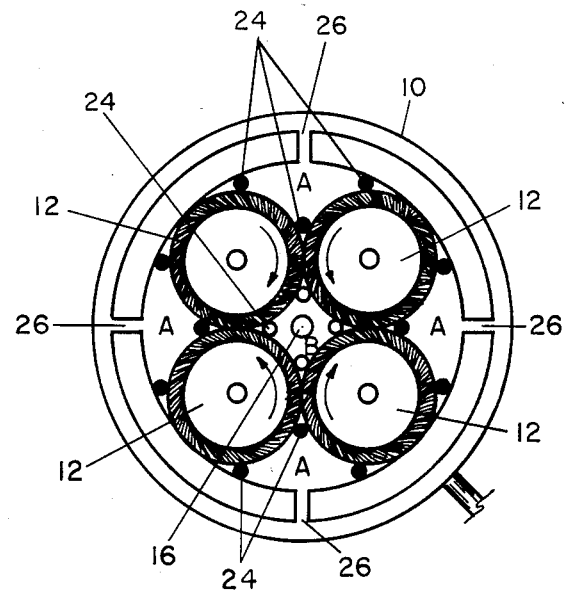
FIG. 1 is a cross section of a desorption apparatus containing four hard rollers which are coated with the sorbent material and which define one sorption zone and four desorption zones.
Figure 4:
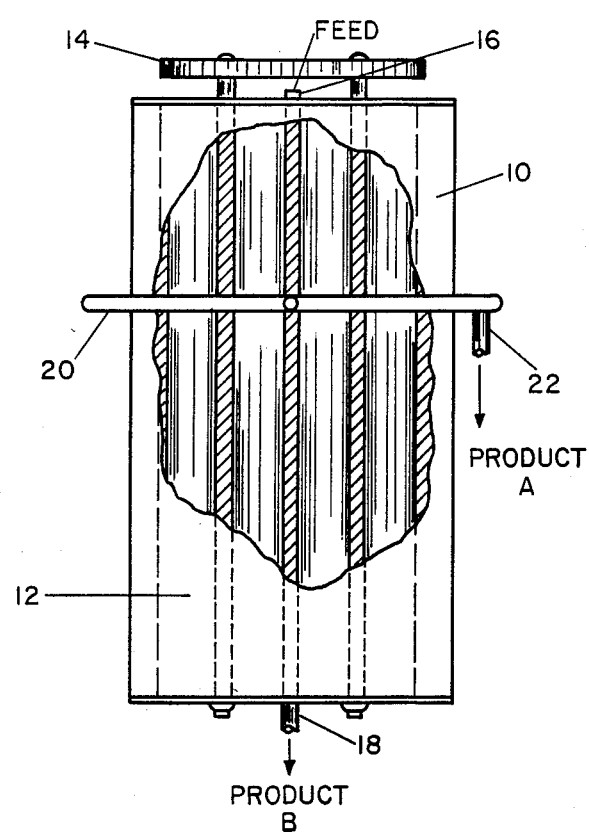
FIG. 4 is a side view of the apparatus of FIG. 1 with a portion of the outer shell removed to show the alignment of the rollers.

FIGS. 1 and 4 illustrate one particular embodiment of the present invention which is comprised of a housing 10 which has four flexible rotating rollers 12 disposed therewithin. The rollers 12 are in series engagement with each other forming a polygonal cylinder. The rollers 12 and the housing 10 thus form a sorption zone B at the center of the rollers 12 and four separate desorption zones A between the rollers 12 and the inside wall of the housing 10. The rotation of the rollers is indicated by the arrows. The rollers are coated with a sorbent material which provides the seal between the sorption and desorption zones. In order to protect the seal between the zones, deformable sealing rollers 24 are provided at the nip of each pair of rollers 12 and also at each nip of the rollers 12 and the inside wall of the housing 10.

Feed fluid enters the apparatus through the sorption zone inlet 16 where it comes into contact with the sorbent material. At least one of the components of the feed fluid is absorbed by the sorbent material in the sorption zone B and then desorbed in desorption zone A after the roller 12 containing the sorbent material rotates into desorption zone A. The separate component leaves desorption zone A through the desorption zone ports 26 which are connected to the desorption manifold 20 and then flow out of the desorption zone outlet 22. The fluid from which the component was absorbed flows out of the sorption zone outlet 18.

FIG. 2 illustrates another embodiment of the present invention wherein six flexible rotating rollers 12 are disposed within a housing 10. The rollers 12 are either formed of a flexible absorbent material or are coated therewith. Again, the sorbent material provides the seal between sorption zone B and desorption zone A. The feed gas enters the sorption zone inlet 16 and the desorbed components exit the apparatus through the desorption zone outlet 22.

Figure 3:
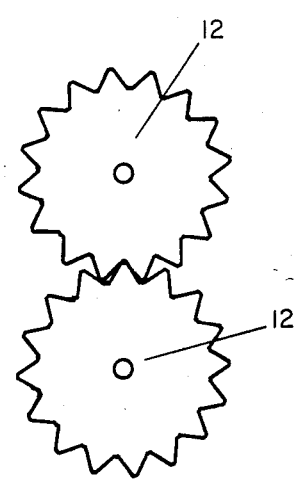
FIG. 3 illustrates another embodiment of the invention wherein the sorbent coated rollers have a gear-like cross section rather than a circular one.

FIG. 3 illustrates a further embodiment of the invention wherein the rollers 12 are not round. Rather, they have a gear-like structure which provides constant contact between the rollers 12 while they are rotating. The rollers can be flexible or inflexible and can either be formed of an absorbent material or coated therewith.

I claim:
1. A continuous process for separating components of a fluid mixture which comprises:
 (a) forming a sorption zone and a desorption zone, said zones being separated by a boundary of a sor- bent material which is disposed on the outside of a plurality of rotating elements and which continuously moves back and forth between the zones, said boundary forming a seal between the zones and said sorbent material or support for the sorbent material being deformable to provide an acceptable seal, (b) causing a fluid mixture to flow into the sorption zone wherein the conditions are such to promote sorption of one of the components of the mixture by the sorbent material, and (c) creating conditions in the desorption zone such that the sorbed component will be desorbed when the sorbent material containing the sorbed component moves into the desorption zone.

2. The process of claim 1 wherein there is disposed between the two zones a series of rotating rollers which have the sorbent material at least on the surface thereof and which are in engagement in series.

3. The process of claim 1 wherein the desorbed component forms a part of a second fluid mixture which is present in the desorption zone.

4. The process of claim 3 wherein the desorption zone is a reaction zone and the rate of reaction is controlled by the amount of desorbed component which enters the desorption zone.

* * * * *